United States Patent [19]

Watson

[11] Patent Number: 4,821,736

[45] Date of Patent: Apr. 18, 1989

[54] HEAD-MOUNTED DEVICE FOR SUPPORTING BREATHING CIRCUIT TUBES AND SENSOR

[75] Inventor: Charles B. Watson, Easton, Conn.

[73] Assignee: Dale Medical Products, Inc., Plainville, Mass.

[21] Appl. No.: 171,896

[22] Filed: Mar. 22, 1988

[51] Int. Cl.$^4$ .............................................. A61B 5/08
[52] U.S. Cl. ................ 128/719; 128/207.17; 128/207.18; 128/DIG. 15; 128/DIG. 26
[58] Field of Search .................. 128/207.17, 207.18, 128/DIG. 26, DIG. 15, 204.22, 716, 718, 719, 791, 419 S; 604/174, 179, 180; 2/171, 181, 181.2, 181.4

[56] References Cited

U.S. PATENT DOCUMENTS

| | | | |
|---|---|---|---|
| 562,765 | 6/1896 | Horton, Jr. ........................ | 128/791 |
| 1,849,745 | 9/1930 | Hoffman ........................... | 128/791 |
| 2,245,969 | 11/1939 | Francisco et al. .......... | 128/DIG. 26 |
| 2,259,817 | 10/1941 | Hawkins ........................ | 128/DIG. 26 |
| 3,029,303 | 4/1962 | Severino ........................ | 128/DIG. 26 |
| 3,659,614 | 5/1972 | Jankelson ........................ | 128/791 |
| 4,018,221 | 4/1977 | Rennie ........................... | 128/207.18 |
| 4,122,857 | 10/1978 | Haerr ........................... | 128/DIG. 26 |
| 4,326,517 | 4/1982 | Whitney et al. ................ | 604/179 |
| 4,524,773 | 6/1985 | Fischell et al. ................ | 128/419 S |

FOREIGN PATENT DOCUMENTS 2107173 4/1983 United Kingdom ................ 2/171

Primary Examiner—Edgar S. Burr
Assistant Examiner—Aaron J. Lewis
Attorney, Agent, or Firm—Wolf, Greenfield & Sacks

[57] ABSTRACT

In a system for monitoring the concentration of $CO_2$ or other gases in a breathing circuit, a device for positioning the $CO_2$ sensor and breathing tubes adjacent the centerline of the forehead and above the head. The device includes a cushion positionable on the forehead, a rigid plate positionable over the cushion and having first and second portions, a band wrapped around the outer surfaces of the first plate portion and cushion and around the head, and connecting means on the second plate portion and sensor for attaching the sensor and breathing circuit tubes adjacent the centerline of the forehead and above the head. The plate counterbalances the weight of the sensor and provides a thermal shield protecting the patient from heat generated by the sensor.

8 Claims, 2 Drawing Sheets

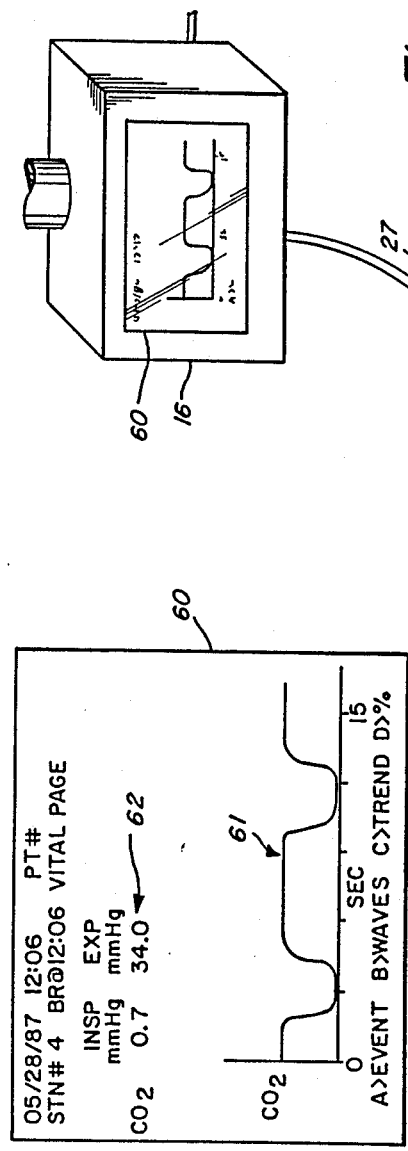
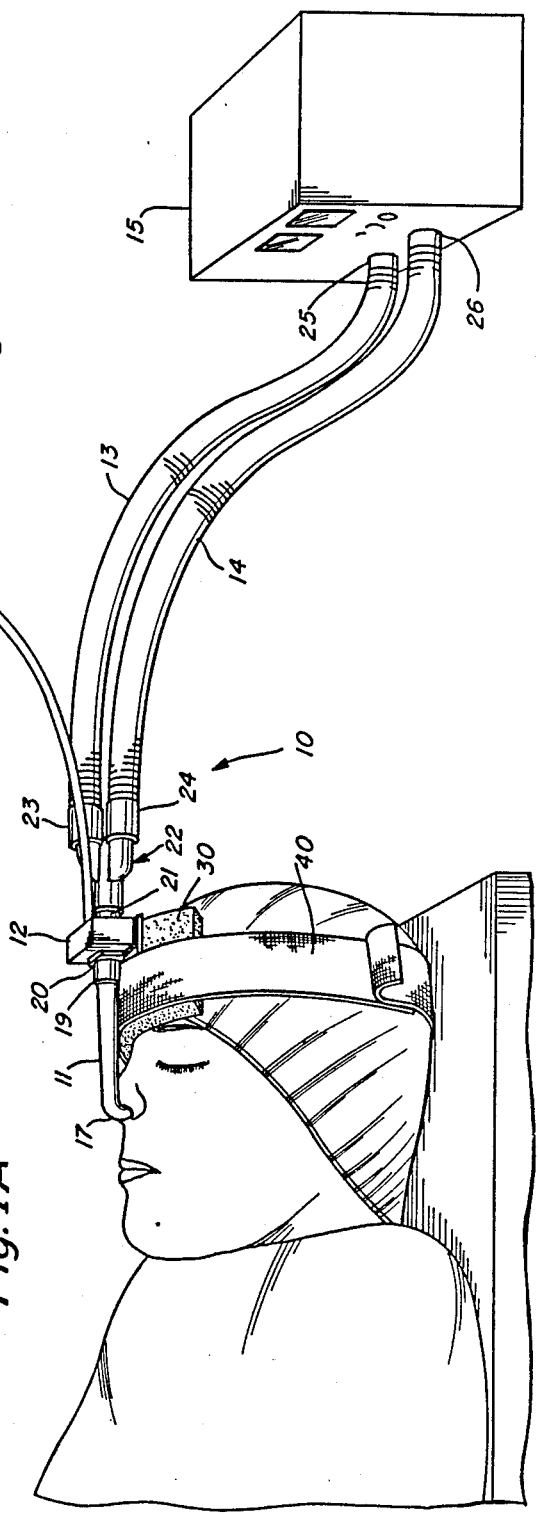
Fig. 1
Fig. 1A

HEAD-MOUNTED DEVICE FOR SUPPORTING BREATHING CIRCUIT TUBES AND SENSOR

BACKGROUND OF THE INVENTION

This invention relates to a head-mounted device for positioning a pair of breathing circuit tubes and a gas sensor.

Capnography is the monitoring of a patient's airway and more specifically, of end-tidal carbon dioxide ($CO_2$) concentration. It is rapidly emerging as the standard procedure for monitoring the adequacy of a patient's ventilation during the administration of anesthetic gases. Capnography is a more reliable indicator of patient ventilation than any qualitative clinical sign, such as chest excursion, observation of a reservoir breathing bag, or auscultation of breathing sounds.

A $CO_2$ capnometer monitors the amount of carbon dioxide gas exhaled by a patient. Carbon dioxide is made in the patient's tissues and is carried by the circulatory system to the lungs. There, it is carried away in alveolar ventilation, mixes with dead space ventilation, and is exhaled. Thus, the output of a capnometer—a capnograph—describes four $CO_2$ related activities: metabolic production; circulation; alveolar ventilation; and dead space ventilation.

A typical $CO_2$ capnograph is shown in FIG. 1A. The graph is a plot of $CO_2$ concentration on the vertical axis and time on the horizontal axis. In a normal patient, inspired carbon dioxide should always be zero. At the beginning of exhalation, the patient's airway carbon dioxide steadily rises toward a relatively flat plateau. After exhalation is completed, carbon dioxide again decreases toward zero.

The $CO_2$ capnometer determines carbon dioxide concentration via infrared absorption at a specific wavelength. The equipment includes a sensor positionable in the breathing circuit. The sensor is connected to a monitor which can be positioned off to the side, away from the patient. In contrast, the sensor needs to be as close as possible to the patient's nose or mouth and integrated with the breathing circuit tubes. The size of the sensor (about the size of a cigarette box), its weight (about 5 lbs.), and the fact that it generates heat (up to about 106° F.), creates problems in positioning the sensor near the patient's face. This is particularly significant during maxillofacial surgery, such as head, neck, oral, or plastic surgery, where it is necessary to leave the neck and face unobstructed so that the surgeon can perform the operation. Not only is it important to keep the face and neck areas clear, but it is important to position the sensor and breathing tubes so that they do not cause the patient irritation and so that they are not easily disconnected or kinked, which would interfere with their operation.

It is an object of this invention to provide an apparatus for supporting a sensor for a breathing circuit.

Another object is to provide a headband mounting device for supporting a sensor and breathing circuit tubes adjacent the centerline of the forehead and up over the head, thereby leaving the face and neck areas clear.

Yet another object is to provide such a device which causes minimum irritation to the patient and prevents dislodgement and kinking of the sensor or tubes.

A further object is to provide such a device which protects the patient from heat generated by a sensor.

SUMMARY OF THE INVENTION

The apparatus of this invention is a device for supporting a sensor and breathing circuit tubes up along the centerline of the forehead and over the head.

In a preferred embodiment, the supporting device is used in a system for monitoring the concentration of a gas, such as $CO_2$, in the patient's airway. The system includes, in serial arrangement, an endotracheal tube, a gas sensor, a pair of breathing circuit tubes, and a breathing machine. The endotracheal tube is positionable in the patient's nose or mouth. The gas sensor has an airway passage fluidly connected between the endotracheal tube and the breathing tube. A measuring element in the sensor determines the concentration of $CO_2$ gas passing through the airway passage. The breathing machine provides a source of inhalation gases to one of the breathing tubes and an exit for exhalation gases from the other breathing tube.

The supporting device includes a foam pad cushion positionable across the forehead, a rigid plate positionable on top of the pad and having upper and lower portions, and an adjustable band stretchable in the lengthwise direction which is wrapped snugly over the pad and lower plate portion and around the back of the head. The upper plate portion extends above the band and has provided thereon connecting elements which mate with connecting elements on the sensor for releasably attaching the sensor to the plate and positioning the sensor adjacent the centerline of the forehead. The plate acts as a thermal barrier preventing heat transfer from the sensor to the patient. The lower plate portion, which is secured by the band, serves as a counterweight to balance the weight of the sensor and the breathing circuit tubes and hold them securely in position.

BRIEF DESCRIPTION OF THE DRAWINGS

FIG. 1 is a schematic view of the apparatus of this invention for supporting a $CO_2$ sensor and breathing circuit tubes adjacent the patient s forehead.

FIG. 1A is an illustration of a typical display screen on a $CO_2$ monitor.

DETAILED DESCRIPTION OF THE PREFERRED EMBODIMENTS

Figure 2:
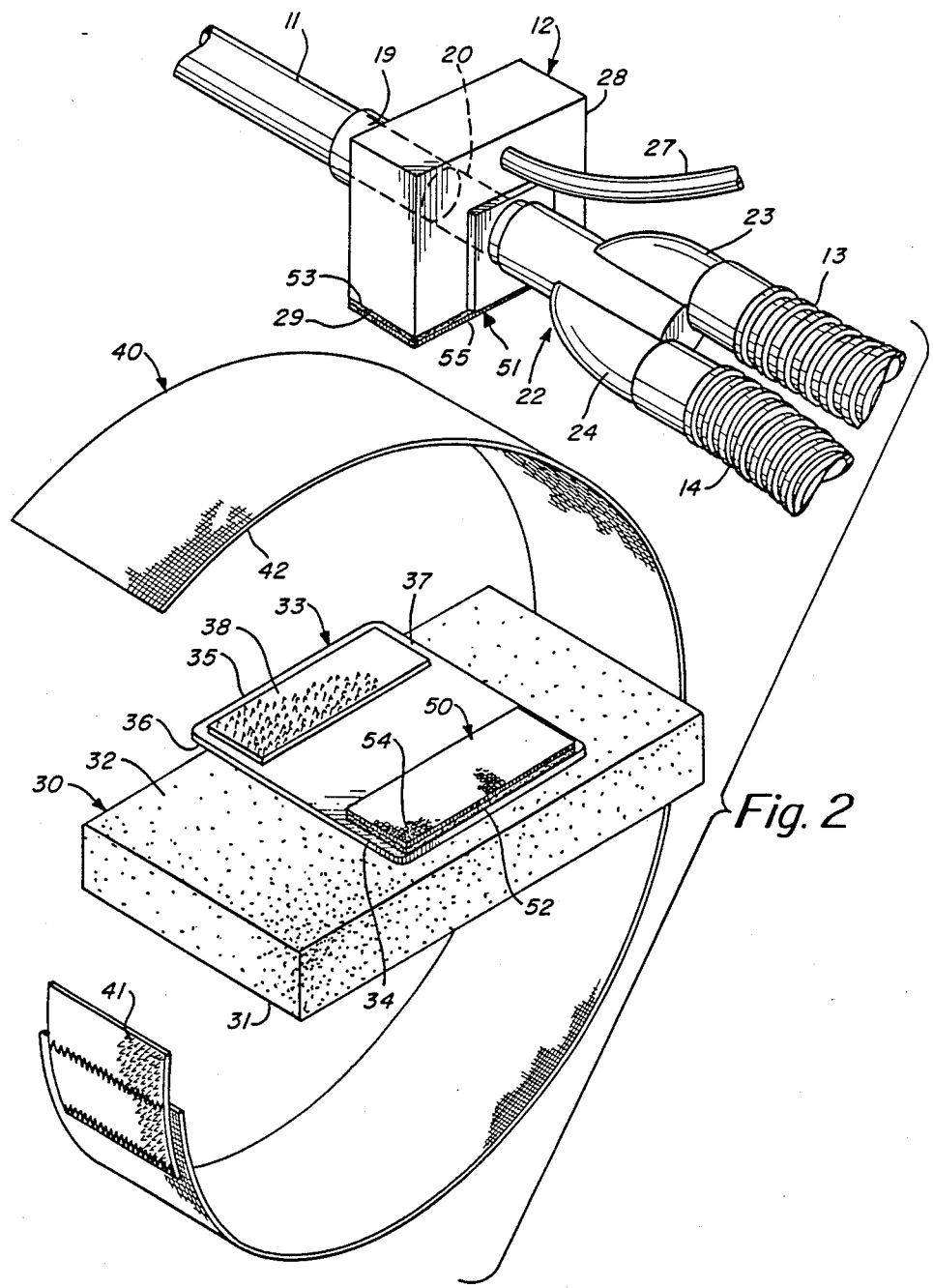
FIG. 2 is an exploded view of the components of the supporting apparatus and adjacent sensor and circuit tubes.

The apparatus of this invention is useful in a system for monitoring the concentration of $CO_2$ gas or other fluids (gas or liquid) present in a breathing circuit. While the preferred embodiment described herein utilizes a $CO_2$ sensor, other fluid sensors which are positionable within a breathing circuit may likewise be used with the supporting apparatus of this invention.

The system 10 of FIG. 1 includes as principle elements, in serial arrangement, an endotracheal tube 11, a sensor 12, a pair of breathing circuit tubes 13, 14, and a breathing machine 15. In addition, a monitor 16 is attached to sensor 12. The distal end of the endotracheal tube 11 has a tube portion 17 inserted in one of the patient's nostrils. A coupler 19 fluidly connects a proximal end of tube 11 and a distal end of an airway passage 20 of sensor 12. Another coupler 21 fluidly connects a proximal end of airway passage 20 and a distal end of a Y-piece 22. Distal ends of circuit tubes 13, 14 are inserted into each of the two proximal branch portions 23, 24 of Y-piece 22. The proximal ends of circuit tubes 13, 14 are fluidly connected to a pair of input ports 25, 26 in breathing machine 15. A tube 27 connects sensor 12 to monitor 16.

The administering gases from machine 15, such as oxygen or anesthesia, are injected into breathing tube 13, which constitutes the inspiratory limb. The exhalation gases from the patient travel from breathing tube 14, the expiratory limb, to the machine 15. There is thus a complete circulatory path between the patient and anesthesia machine. The $CO_2$ sensor 12 is fluidly connected between the circuit tubes 13, 14 and endotracheal tube 11 for monitoring the inhalation and exhalation gases from the patient.

The system is positioned as shown in FIG. 1. Endotracheal tube 11 exits from the patient's nose and extends along the longitudinal centerline of the nose and between the eyes. The sensor 12 is positioned along the longitudinal centerline of the forehead with the airway passage 20 positioned above the centerline of the forehead and the breathing circuit tubes 13, 14 extend straight over the head.

The component parts of this invention for thus supporting the sensor and circuit tubes are shown in FIG. 2. They include cushion 30, rigid plate 33, headband 40, and two mushroom connecting members 50, 51. Cushion 30 is a polyurethane foam pad about six inches long, about three inches high, and about one inch thick. It is positioned lengthwise across the forehead with an inner surface 31 placed on the forehead and on opposing outer surface 32. On top of outer surface 32 and aligned with the centerline of the forehead is plate 33 having upper 34 and lower 35 portions. Plate 33 is a substantially rigid plastic sheet about three to four inches square and 1/16" thick, having inner surface 36 and outer surface 37. It is of sufficient density and thickness to act as a thermal barrier and preferably is made of a material such as polypropylene, polystyrene, an ionomer (e.g., SURLYN, sold by E. I. DuPont de Nemours & Co., Wilmington, Del.), polyethylene, or polyurethane Headband 40 is a two and one-half inch wide polyester covered elasticized band having an adjustable fastener at one end. The fastener constitutes a male VELCRO element 41 which is releasably attachable to a nap 42 on the surface of band 40. Another male VELCRO element 38 is attached to the outer surface 37 of lower plate portion 35 for releasable attachment to the nap 42 on band 40. The band 40 is placed over the exposed surfaces 32 of pad 30, 37 of plate 33 and VELCRO element 38 and is then stretched lengthwise, wrapped securely around the head, and attached to itself with a fastener 41 to thereby secure the plate and pad firmly in position on the forehead.

The upper plate portion 34 extends above the band 40 and has positioned thereon a first mushroom connector 50 which is releasably attachable to a second mushroom connector 51 attached to housing 28 of sensor 12. Connectors 50, 51 are preferably thin plastic sheets with an adhesive backing and having rigid plastic connecting hooks 54, 55 projecting from their front surfaces. Sheets of such mushroom hook connectors are sold by Consumer Care Products, Sheboyagan Falls, Wisc., under the name POLYLOK. The adhesive backing 52 of first connector 50 is attached to the outer surface of upper plate portion 34 and the adhesive backing 53 of second connector 52 is attached to the bottom surface 29 of sensor housing 28. The mushroom hooks 54, 55 of the first and second connectors are then brought together in face-to-face relationship to provide a rigid, secure, and releasable connection for supporting the sensor above the centerline of the forehead. The rigid plastic plate provides a platform to counterbalance the weight of the sensor and acts as a thermal barrier protecting the patient from the heat generated by the sensor.

The breathing tubes 13, 14 are positioned away from the neck and cheek area of the face and when used with nasal intubation (wherein the endotracheal tube extends from the nose), the supporting device of this invention is of great advantage for maxillofacial surgery. The tubes 11, 13, 14 are positioned out of the way so that they can not be pulled apart, dislodged, or kinked. The sensor 12 and tubes are held securely along the patient's forehead without pulling on or otherwise irritating any part of the patient.

Within housing 28 of sensor 12 is a transducer element (not shown) for monitoring the $CO_2$ concentration within the airway passage 20. The electrical output signal from the transducer is sent via cable 27 to monitor 26 which contains a measuring circuit (not shown) and a display screen 60. Display screen 60, as shown in FIG. 1A, provide a continuous graphical display 61 of $CO_2$ concentration as a function of time as well as a digital display 62 of the current inspiration and expiration $CO_2$ readings in mmHg. The sensor system may be, for example, the Model 1260 End Tidal $CO_2$ Monitor sold by Novametrix Medical Systems, Inc., Wallingford, Conn., the HP 14360 $CO_2$ Transducer with Cafstick sold by Hewlett Packard, Waltham, Mass., or a similar system sold by Siemens-Elema Ventilator Systems, Schaumberg, Ill.

While a preferred embodiment of the invention has hereinbefore been described, it is appreciated that variations thereof will be perceived by those skilled in the art, which variations are nevertheless within the scope of the invention as defined by the claim appended hereto.

What is claimed is:

1. In a system for monitoring the concentration of fluids such as $CO_2$ in a breathing circuit of the type including an endotracheal tube positionable in a patient's nose or mouth, a fluid sensor having an airway passage means connected to the endotracheal tube and having means for measuring the concentration of a fluid which passes through the airway passage means, a pair of breathing tubes connected to the airway passage means, and a breathing machine providing a source of inhalation fluids to one of the breathing tubes and an exit for exhalation fluids from the other breathing tube, a device for supporting the breathing tubes and sensor comprising:

a cushion positionable across the forehead;

a plate positionable over the cushion and having first and second plate portions, said plate being substantially rigid and providing a thermal insulating barrier;

a band stretchable in the lengthwise direction and adapted to be wrapped snugly over the cushion and the first plate portion and around the back of the head, the band having adjustable and releasable attaching means for securing the band in said wrapped position;

the second plate portion extending above the band; and connecting means on the second plate portion and on the sensor for attaching the sensor to the second plate portion;

wherein the plate acts as a thermal barrier reducing heat transfer from the sensor to the patient and counterbalances the weight of the sensor so that the sensor is supported in a substantially fixed position on the plate adjacent the centerline of the patient s forehead and the circuit tubes are positioned up over the patient's head.

2. The device of claim 1, wherein the connecting means includes rigid plastic mating hooks provided on each of the second plate portion and on the sensor for releasably connecting the same.

3. The device of claim 2, wherein the connecting means further includes an adhesive backing for attaching the connecting means to each of the second plate portion and sensor.

4. The device of claim 2, wherein the plate is a substantially rigid plastic plate.

5. The device of claim 2, wherein the band is at least about two inches in width.

6. The device of claim 5, wherein the second plate portion extends at least about one inch above the band.

7. The device of claim 6, wherein the band is a covered elasticized band.

8. The device of claim 7, wherein the band includes releasable VELCRO fastening means.

* * * * *

UNITED STATES PATENT AND TRADEMARK OFFICE
CERTIFICATE OF CORRECTION

PATENT NO. :  4,821,736
DATED      :  April 18, 1989
INVENTOR(S) : Watson

It is certified that error appears in the above—identified patent and that said Letters Patent is hereby corrected as shown below:

Col. 4, line 21 - delete "26" and change to -- 16 --.

Col. 5, line 6 - delete "patient s" and change to -- patient's

Signed and Sealed this

Ninth Day of January, 1990

Attest:

JEFFREY M. SAMUELS

Attesting Officer     Acting Commissioner of Patents and Trademarks